(12) United States Patent
Slagel

(10) Patent No.: US 11,013,709 B2
(45) Date of Patent: May 25, 2021

(54) HIGHLY PURIFIED EICOSAPENTAENOIC ACID, AS FREE FATTY ACID, REDUCES FECAL CALPROTECTIN LEVELS AND PREVENTS CLINICAL RELAPSE IN ULCERATIVE COLITIS PATIENTS

(71) Applicant: S.L.A. PHARMA AG, Liestal (CH)

(72) Inventor: Justin Slagel, Hertfordshire (GB)

(73) Assignee: S.L.A. PHARMA AG, Liestal (CH)

( * ) Notice: Subject to any disclaimer, the term of this patent is extended or adjusted under 35 U.S.C. 154(b) by 0 days.

(21) Appl. No.: 16/535,536

(22) Filed: Aug. 8, 2019

(65) Prior Publication Data

US 2019/0365691 A1 Dec. 5, 2019

Related U.S. Application Data

(63) Continuation-in-part of application No. PCT/IB2018/000168, filed on Feb. 6, 2018.

(60) Provisional application No. 62/456,816, filed on Feb. 9, 2017.

(51) Int. Cl.
*A61K 31/202* (2006.01)
*A61P 1/04* (2006.01)
*A61K 45/06* (2006.01)
*A61P 1/00* (2006.01)

(52) U.S. Cl.
CPC ............ *A61K 31/202* (2013.01); *A61K 45/06* (2013.01); *A61P 1/00* (2018.01); *A61P 1/04* (2018.01)

(58) Field of Classification Search
CPC ................................ A61K 31/202; A61P 1/04
See application file for complete search history.

(56) References Cited

U.S. PATENT DOCUMENTS

2016/0000740 A1* 1/2016 Zhang ................... A61K 31/202
424/456

FOREIGN PATENT DOCUMENTS

WO WO2006067498 A1 6/2006
WO WO-2014158256 A1 * 10/2014 ........... A61K 31/232
WO WO2015104414 A1 7/2015

OTHER PUBLICATIONS

Wang et al., "Oral 5-aminosalicylic acid for induction of remission in ulcerative colitis," Cochrane Database of Systematic Reviews 2016, Issue 4. Art. No. CD000543. (Year: 2016).*
Grimstad et al., "Salmon diet in patients with active ulcerative colitis reduced the simple clinical colitis activity index and increased the anti-inflammatory fatty acid index—a pilot study," Scand. J. Clin. Lab. Invest. Feb. 2011;71(1):68-73. PMID: 21142420. (Year: 2011).*
Lasson et al., "Pharmacological intervention based on fecal calprotectin levels in patients with ulcerative colitis at high risk of a relapse: A prospective, randomized, controlled study," United European Gastroenterol. J. Feb. 2015;3(1):72-79. PMID: 25653861. (Year: 2015).*
Ananthakrishnan, Ashwin N. et al. Long-term intake of dietary fat and risk of ulcerative colitis and Crohn's disease. *Gut* 2014; 63: 776-784.
Belluzzi, A. et al. Effects of new fish oil derivative on fatty acid phospholipid-membrane pattern in a group of Crohn's disease patients. *Dig Dis Sci* 1994; 39: 2589-2594.
Calder, Philip C. Marine omega-3 fatty acids and inflammatory processes: Effects, mechanisms and clinical relevance. *Biochim Biophys Acta* 2015; 1851: 469-484.
Cheifetz, Adam S. et al. Complementary and Alternative Medicines used by Patients with Inflammatory Bowel Diseases, *Gastroenterology* 2017; 152:415-429.
Costa, F. et al. Calprotectin is a stronger predictive marker of relapse in ulcerative colitis than in Crohn's disease. *Gut* 2005; 54: 364-368.
Daperno, Marco et al. Results of the 2nd part Scientific Workshop of the ECCO (II): Measures and markers of prediction to achieve, detect, and monitor intestinal healing in Inflammatory Bowel Disease. *J Crohns Colitis* 2011; 5: 484-498.
Davidson, Michael H. et al. A novel omega-3 free fatty acid formulation has dramatically improved bioavailability during a low-fat diet compared with omega-3-acid ethyl esters: the ECLIPSE (Epanova® compared to Lovaza®) in a pharmacokinetic single-dose evaluation) study. *J Clin Lipidol* 2012; 6: 573-584.
De Ley, M, et al. Fish oil for induction of remission in ulcerative colitis. Cochrane Database Syst Rev 2007; (4):CD005986.
De Silva, Punyanganie S.A. et al. An Association Between Dietary Arachidonic Acid, Measured in Adipose Tissue, and Ulcerative Colitis, *Gastroenterology* 2010; 139-:1912-1917.
El Boustani, S. et al. Enteral absorption in man of eicosapentaenoic acid in different chemical forms. *Lipids* 1987; 22: 711-714.
Feagan, Brian G. et al Omega-3 free fatty acids for the maintenance of remission in Crohn disease: the EPIC Randomized Controlled Trials. *JAMA* 2008; 299: 1690-1697.
García-Sánchez, Valle et al. Does fecal calprotectin predict relapse in patients with Crohn's disease and ulcerative colitis? *J Crohns Colitis* 2010; 4: 144-152.
Geboes, K. et al. A Reproducible Grading Scale for Histological Assessment of Inflammation in Ulcerative Colitis, *Gut* 2000; 47:404-409.
Guardiola, Jordi et al. et al. Fecal Level of Calprotectin Identifies Histologic Inflammation in Patients With Ulcerative Colitis in Clinical and Endoscopic Remission. *Clin Gastroenterol Hepatol* 2014, 12: 1865-1870.

(Continued)

*Primary Examiner* — Theodore R. Howell
(74) *Attorney, Agent, or Firm* — Tristan A. Fuierer; Marianne Fuierer; Olive Law Group, PLLC

(57) ABSTRACT

The present invention relates to a method of administering an effective dose of highly purified eicosapentaenoic acid as free-fatty acid (EPA-FFA) to reduce fecal calprotectin levels and reduce the risk of clinical relapse in UC patients. The eicosapentaenoic acid, in the free fatty acid (EPA-FFA) form, has a purity of at least 95%, and more preferably at least 99%.

15 Claims, No Drawings

(56) References Cited

OTHER PUBLICATIONS

Langholz, E. et al. Munkholm P, Davidsen M, et al. Course of ulcerative colitis: Analysis of changes in disease activity over years. *Gastroenterology* 1994; 107: 3-11.

Lee, Dale et al. Diet in the pathogenesis and treatment of inflammatory bowel diseases. *Gastroenterology* 2015; 148: 1087-1106.

Lev-Tzion, R. et al. Omega 3 fatty acids (fish oil) for maintenance of remission in Crohn's disease. Cochrane Database Syst Rev 2014; (2): CD006320.

Lewis, James D. et al. Diet as a Trigger or Therapy for Inflammatory Bowel Diseases. *Gastroenterology* 2017; 152: 398-414.

Lobatón, Triana et al. A New Rapid Quantitative Test for Fecal Calprotectin Predicts Endoscopic Activity in Ulcerative Colitis. *Inflamm Bowel Dis* 2013; 19: 1034-1042.

MacLean, Catherine H. et al. Systematic review of the effects of n-3 fatty acids in inflammatory bowel disease. *Am J Clin Nutr* 2005; 82: 611-619.

Marion-Letellier, Rachel et al. Polyunsaturated fatty acids in inflammatory bowel diseases: a reappraisal of effects and therapeutic approaches. *Inflamm Bowel Dis* 2013; 19: 650-661.

Molander, Pauliina et al. Does fecal calprotectin predict short-term relapse after stopping TNFα-blocking agents in inflammatory bowel disease patients in deep remission? *J Crohns Colitis* 2015; 9: 33-40.

Mooiweer, E. et al. Low fecal calprotectin predicts sustained clinical remission in inflammatory bowel disease patients: a plea for deep remission. *J Crohns Colitis* 2015; 9: 50-55.

Prossomariti, A. et al. Eicosapentaenoic acid-free fatty acid supplementation for the prevention of colitisassociated colorectal cancer: a phase 1 clinical trial. United European Gastroenterology Journal 2016, 4(5): A240.

Prossomariti, A. et al. Short-term treatment with eicosapentaenoic acid improves inflammation and affects colonic differentiation markers and microbiota in patients with ulcerative colitis. *Sci Rep* 2017; 7: 7458.

Sahmoud, T. et al. Identifying patients with a high risk of relapse in quiescent Crohn's disease. The GETAID Group. The Groupe d'Etudes Thérapeutiques des Affections Inflammatoires Digestives. *Gut* 1995; 37: 811-818.

Sandborn, W.J. et al. Correlation between concentrations of fecal calprotectin and outcomes of patients with ulcerative colitis in a phase 2 trial. *Gastroenterology* 2016; 150: 96-102.

Scaioli, E. et al. Clinical application of faecal calprotectin in ulcerative colitis patients. *Eur J Gastroenterol Hepatol* 2015; 27: 1418-1424.

Scaioli, E. et al. The pharmacokinetic profile of a new gastroresistant capsule preparation of eicosapentaenoic acid as the free fatty acid. *BioMed Res Int* 2015; 2015: 360825.

Scaioli, E. et al. Highly purified eicosapentaenoic acid, as free fatty acid, reduces fecal calprotectin levels and prevents clinical relapse in ulcerative colitis patients: a double-blind randomized, placebo controlled trial. *Journal of Crohn's and Colitis* 2017, 11:supp. S376-S376.

Schroeder, K.W. et al. Coated Oral 5-Aminosalicylic Acid Therapy for Mildly to Moderately Active Ulcerative Colitis. *N Engl J Med* 1987; 317: 1625-1629.

Sipponen, T. et al. Fecal calprotectin in diagnosis and clinical assessment of inflammatory bowel disease. *Scand J Gastroenterol* 2015; 50: 74-80.

Turner, D. et al. Maintenance of remission in inflammatory bowel disease using omega-3 fatty acids (fish oil): a systematic review and meta-analyses. *Inflamm Bowel Dis* 2011; 17: 336-345.

Vermeire, S. et al. Laboratory markers in IBD: useful, magic, or unnecessary toys? *Gut* 2006; 55: 426-431.

Yaqoob, P. Mechanisms underlying the immunomodulatory effects of n-3 PUFA. *Proc Nutr Soc* 2010; 69: 311-315.

Zenlea, T. et al. Histology Grade Is Independently Associated With Relapse Risk in Patients With Ulcerative Colitis in Clinical Remission: A Prospective Study. *Am J Gastroenterol* 2016; 111: 685-690.

\* cited by examiner

HIGHLY PURIFIED EICOSAPENTAENOIC ACID, AS FREE FATTY ACID, REDUCES FECAL CALPROTECTIN LEVELS AND PREVENTS CLINICAL RELAPSE IN ULCERATIVE COLITIS PATIENTS

CROSS REFERENCE TO RELATED APPLICATIONS

The present application is a Continuation-in-Part application and claims priority to copending International Application No. PCT/IB2018/000168 filed on Feb. 6, 2018, which in turn claims priority U.S. Provisional Patent Application Ser. No. 62/456,816, filed on Feb. 9, 2017.

BACKGROUND OF THE INVENTION

Technical Field

This invention relates to the use of highly purified eicosapentaenoic acid as free fatty acids (EPA-FFA) for reducing fecal calprotectin (FC) levels and relapses in subjects with ulcerative colitis.

Related Art

Ulcerative colitis (UC) is a chronic inflammatory condition affecting the colon, characterized by alternating periods of activity and remission.[1] Clinical activity is frequently preceded by a progressive asymptomatic mucosal inflammation. Effective treatment of the pre-clinical condition may prevent clinical relapses and can potentially play a key role in the management of UC.

Fecal calprotectin (FC), a 36-kilodalton calcium- and zinc-binding protein, comprises up to 60% of the total cytosolic protein in granulocytes. It is stable in feces for up to 7 days, correlates well with fecal granulocyte excretion and is a useful marker of mucosal inflammation in inflammatory bowel disease (IBD) patients.[2] Specifically, in patients with UC, FC levels higher than 150 µg/g is associated with endoscopic[3] and histological activity[4] and can predict clinical relapse[5-7].

The long chain dietary n-3 polyunsaturated fatty acids (PUFAs), in particular eicosapentaenoic acid (EPA, the major component of n-3 fish oil), are beneficial in several chronic inflammatory disorders.[8] EPA is involved in the regulation of immunological and inflammatory responses. It modulates the composition of cell membranes by displacing n-6 PUFAs, influences lipid raft formation in cell signaling,[9] and leads to the production of anti-inflammatory mediators, such as resolvins, defensins and maresins.[8]

Despite the experimental evidence implying biological plausibility for the role of n-3 PUFAs in inflammatory bowel disease (IBD), the clinical data about the effectiveness of n-3 PUFAs in IBD are still controversial and conflicting, especially in Crohn's disease (CD).[10-12] Notably, recent epidemiological studies suggest that n-3 PUFAs may protect against the development of UC.[13-15] but the results are contradictory.

Accordingly, there is a need for a more potent and active omega-3 PUFA which also exhibits greater in vivo stability and purity. Specifically there is the need for the use of an isolated and purified omega-3 PUFA in free fatty acid form that has the ability to reduce levels of fecal calprotectin and relapses in subjects with ulcerative colitis.

SUMMARY OF THE INVENTION

The present invention relates to showing the effectiveness of highly purified eicosapentaenoic acid as free-fatty acid (EPA-FFA) in reducing fecal calprotectin levels and preventing recurrence in a group of asymptomatic UC patients at risk of clinical relapse, defined as fecal calprotectin level ≥150 µg/g. Preferably, the eicosapentaenoic acid in the free fatty acid (EPA-FFA) form has a purity of at least 90%, and more preferably at least 95% and most preferred at least 99%.

In one aspect, the present invention provides a method of reducing fecal calprotectin levels and relapses in subjects with ulcerative colitis in a subject by administering to the subject EPA-FFA having a purity of at least 90%, and more preferably at least 95% and most preferred at least 99%, in an amount effective to reduce levels of fecal calprotectin below 150 µg/g and more preferably below 110 µg/g of fecal matter and most preferably a reduction of FC of about 100 µg/g or greater over a six month period. Importantly the present invention has shown a reduction of at least 100 µg/g of FC over a six month period of administering highly purified EPA-FFA as shown in the results. The purified EPA-FFA can be administered with or without a pharmaceutically acceptable carrier.

In another aspect, the present provides a method of reducing fecal calprotectin levels and relapses in subjects with ulcerative colitis in a subject by administering to the subject EPA-FFA having a purity of at least 90%, and more preferably at least 95% and most preferred at least 99%, in a therapeutic amount effective to reduce levels of fecal calprotectin below 150 µg/g and more preferably below 110 ug/g and most preferably below 85 ug/g of fecal matter over a six month period alone or in combination with another therapeutic agent used to treat UC. The therapeutic agent that may be combined with the EPA-FFA may include aminosalicylates (5-ASA), such as, sulfasalazine, mesalamine, olsalazine, and balsalazide; corticosteroids, such as, prednisone, methylprednisolone and budesonide; immunomodulators; antibiotics such as, metronidazole, ampicillin, ciprofloxacin, and etc.; and biologic therapies such as antibodies.

In yet another aspect, the present invention provides for a composition comprising EPA-FFA having a purity of at least 90%, and more preferably at least 95% and most preferred at least 99%, in a therapeutic amount effective to reduce levels of fecal calprotectin below 150 µg/g and more preferably below 110 ug/g of fecal matter alone or in combination with another therapeutic agent used to treat UC. The therapeutic agent that may be combined with the EPA-FFA may include aminosalicylates (5-ASA), such as, sulfasalazine, mesalamine, olsalazine, and balsalazide; corticosteroids, such as, prednisone, methylprednisolone and budesonide; immunomodulators; antibiotics such as, metronidazole, ampicillin, ciprofloxacin, and etc.; and biologic therapies such as antibodies.

In a still further aspect, the present invention provides for use of a composition comprising EPA-FFA having a purity of at least 90%, and more preferably at least 95% and most preferred at least 99%, in a therapeutic amount effective to reduce levels of fecal calprotectin below 150 µg/g and more preferably below 110 ug/g of fecal matter. Preferably the therapeutic amount is from about 250 mg per day to 4 grams per day and more preferably from about 1000 mg to about 2 g daily. Additionally, the EPA-FFA can be combined with aminosalicylates (5-ASA), such as, sulfasalazine, mesalamine, olsalazine, and balsalazide; corticosteroids, such as, prednisone, methylprednisolone and budesonide; immunomodulators; antibiotics such as, metronidazole, ampicillin, ciprofloxacin, and etc.; and biologic therapies such as antibodies.

In another aspect, the present invention provides a method to reduce the amount of Fecal calprotectin (FC) by about 100 µg/g or more over a period of six month period relative to the amount of FC determined in a patient having a level of FC greater than about 150 µg/g to about 200 µg/g before administering highly purified EPA-FFA. The EPA-FFA having a purity of at least 90%, and more preferably at least 95% and most preferred at least 99% and in a therapeutic amount from about 250 mg per day to 4 grams per day and more preferably from about 1000 mg to about 2 g daily.

Still further, the present invention provides for the use of highly purified EPA-FFA to reduce the amount of Fecal calprotectin (FC) by about 100 µg/g or more over a period of six month period relative to the amount of FC determined in a patient having a level of FC greater than about 150 µg/g to about 200 µg/g before administering highly purified EPA-FFA. The EPA-FFA having a purity of at least 90%, and more preferably at least 95% and most preferred at least 99% and in a therapeutic amount from about 250 mg per day to 4 grams per day and more preferably from about 1000 mg to about 2 g daily.

These and other advantages and features of the present invention will be described more fully in a detailed description of the preferred embodiments which follows.

DETAILED DESCRIPTION OF THE INVENTION

The prevention of clinical relapse represents the major outcome in the treatment of ulcerative colitis (UC) patients. High fecal calprotectin levels indicate mucosal inflammation and have been shown to predict clinical relapse in many groups of UC patients. Recent epidemiological studies suggest that n-3 polyunsaturated fatty acids protect against the development of UC. Eicosapentaenoic acid, the major component of n-3 fish oil, has shown to have anti-inflammatory properties in chronic inflammatory disorders. The aim of this present invention was to define the effectiveness of highly purified eicosapentaenoic acid as free-fatty acid (EPA-FFA) in reducing fecal calprotectin levels and preventing recurrence in a group of asymptomatic UC patients at risk of clinical relapse, defined as fecal calprotectin level ≥150 m/g.

It was found, as shown herein, that a placebo-controlled trial of 60 patients with UC treated for 6 months with the administration of highly purified EPA-FFA reduced fecal levels of calprotectin with no serious adverse events. As such, highly purified EPA-FFA is effective in reducing the amount of fecal calprotectin FC in treated patients and such use may also have the ability to test for effectiveness and to identify symptom-free remission in patients with UC using the highly purified EPA-FFA.

The present invention is based on the findings that administration of EPA-FFA is effective in vivo in inhibiting or reducing levels of fecal calprotectin.

Preferably, the EPA-FFA used for making the medical preparations, medicaments or compositions in accordance with the invention is of at least about 90% purity and will contain no more than minimal or pharmaceutically insignificant amounts of any other polyunsaturated fatty acids. A purity of more than 95% is recommended with the highest commercially available grade (about 99% purity), which is substantially free of any other polyunsaturated fatty acids, being the most preferred material.

Thus, according to one aspect of the present invention, highly purified eicosapentaenoic acid as a free fatty acid is used to make a medical preparation or medicament for the reduction of fecal calprotectin in a treated subject.

EPA may be found in fish oil, plants or microorganisms as free fatty acids or in conjugated forms such as acylglycerols, phospholipids, sulfolipids or glycolipids, and may be extracted through a variety of means well-known in the art. Such means may include extraction with organic solvents, such as methanol and chloroform, sonication, supercritical fluid extraction using for example carbon dioxide, and physical means such as presses, or combinations thereof. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Protecting groups may be removed at any step. Desirably, purification of fractions containing EPA may be accomplished by initial esterfication, treatment with urea, supercritical fluid extraction and chromatography with the subsequent isolation of the free fatty acid.

In order to isolate EPA from the triglyceride it is necessary to free the fatty acids by hydrolysis or ester exchange in order that purification can be effective. Purification can be achieved by techniques such as fractional distillation, molecular distillation and chromatography. A particularly desirable chromatographic method employs super-critical fluids using, for example, carbon dioxide as the mobile phase, such as described in European Patent EP 0 712 651. It has been found that using such techniques EPA may be purified to levels approaching 100 percent. For practical reasons the EPA may be purified as its ethyl or methyl ester and hydrolyzed back to the free fatty acid form. Purification enables a product to be prepared which is highly concentrated and free from other fatty acids that are less desirable in the finished product. In addition other chemicals entities such as mono- and di-glycerides, hydrocarbons, pesticide residues and the like can be removed. The highly purified EPA is thus suitable for human ingestion as it contains substantially reduced levels of toxins, compounds contributing to unpalatability or undesirable fatty acids such as saturated fatty acids. The free fatty acid form of EPA can be absorbed in the gut easily without need of prior enzymatic conversion. Using this method about 150 kg of unpure EPA can be converted into 50 kg of essentially pure EPA-FFA, that being at least 90% purity.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Protecting groups may be removed at any step. Desirably, purification of fractions containing EPA may be accomplished by initial esterfication, treatment with urea, supercritical fluid extraction and chromatography with the subsequent isolation of the free fatty acid.

A preferred EPA free fatty acid is commercially available under the tradename ALFA™ (S.L.A. Pharma, UK). This PUFA is 99% pure EPA, in a free fatty acid form and formulated into a pH-dependent, enteric-coated capsules designed to ensure release of the contents in the small intestine at pH 5.5. Other constituents include AA (≤0.5%) and trace amounts of other fatty acids. Key advantages of this preparation of EPA are its high degree of purity compared with many fish oil products, its presentation as the free fatty acid maximizing systemic bioavailability, ease of dosage in 500 mg capsules and a delayed-release profile, which minimizes gastro-intestinal side-effects.

Preferably the 99% pure EPA-FFA is administered in an amount from about 250 mg to 4 g per day and more preferably from about 1000 mg to about 2 g daily. The dosage may be preferably administered daily, but depending on the dosage may be extended to every other day, weekly or longer for about 1 to 8 months. Notably, the tolerability of 99% pure EPA as ALFA™ capsules is excellent and the predominant small bowel delivery of EPA minimized any unpleasant taste and smell sensations that have previously hampered therapy with other fish oil preparations.

The EPA-FFA alone or in combination with another therapeutic agent used to treat UC may be formulated in multiple delivery modes. The active agent can be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

A solid composition form may include a solid carrier and one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredients. In tablets, the active ingredients are mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution); alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Having described the invention in detail, it will be apparent that modifications and variations are possible without departing the scope of the invention defined in the appended claims. Furthermore, it should be appreciated that the following examples are provided as non-limiting examples.

The present invention provides for a double-blind, randomized, placebo-controlled study with UC patients with fecal calprotectin level ≥150 µg/g and in stable therapy for at least the 3 previous months. Each subject, receives either 2 grams daily of EPA-FFA (2 dosages of 500 mg sustained-release capsules, twice a day) or placebo (2 dosages of 500 mg sustained-release capsules of capric and caprylic acids, twice daily) for a 6 month period. At baseline, the patients undergo a total colonoscopy. Fecal calprotectin levels, clinical and laboratory assessments are performed at baseline, 3 and 6 months or at the time of clinical relapse, which has been defined as the occurrence of symptoms accompanied by an increase in the partial Mayo score ≥2 and/or requiring a change in therapy.

Fecal calprotectin levels will decrease in the EPA-FFA group in comparison to the placebo group. Thus, EPA-FFA decreases fecal calprotectin levels and is a safe and acceptable treatment to maintain symptom-free remission in UC patients.

Eligible patients will be 18 years and older with a diagnosis of UC based on clinical, endoscopic and histological criteria, in stable clinical remission, defined as partial Mayo score <2 for at least the last 3 months,[16] with a degree of mucosal activity defined as FC levels ≥150 µg/g. Use of concomitant therapies for UC (such as oral mesalazine, immunomodulators and/or biological drugs) without modification in the previous 3 months is allowed. Exclusion criteria were: 1) recent use of steroids (<3 months), topical mesalazine (<3 months) or other experimental drugs (<3 months); 2) concomitant use of non-steroidal anti-inflammatory drugs and/or anticoagulants; 3) proctitis; 4) pregnancy or breast feeding; 5) known or suspected hypersensitivity to EPA or n-3 PUFAs; and 6) severe comorbidities (serious cardiopulmonary, hepatic, renal, neurological, psychiatric disease, diabetes or hemorrhagic disorders).

Patients who satisfied the inclusion criteria undergo blood tests, including C-reactive protein (CRP) (normal upper limit 5 mg/L) and a total colonoscopy with multiple biopsies at baseline. They are then randomized 1:1 to receive either 2 g daily of EPA-FFA (2×500 mg gastro-resistant sustained-release capsules, twice-daily) or 2 g of placebo (2×500 mg gastro-resistant sustained-release capsules of capric and caprylic acids that are triglycerides of the fractionated plant fatty acids, twice-daily) for a 6-month period. The entire study team are blinded to the treatment assignment.

The primary endpoint is the proportion of patients achieving a 100-point reduction (100 µg/g or greater) from baseline in FC level at 6 months. The secondary endpoint is the number of patients achieving maintenance of clinical remission at 6 months, defined as a stable partial Mayo score <2 without any change in therapy. A combined endpoint consisting of the number of patients achieving the primary and secondary endpoints is also calculated.

Clinical assessments, FC measurement and blood tests are repeated at 3 and 6 months, or at the time of clinical relapse, which was defined as the occurrence of symptoms accompanied by an increase in the partial Mayo score ≥2 and requiring a change in therapy.

Fecal calprotectin analyses are performed during the screening phase, and at 3 and 6 months, or at the time of clinical relapse (24 h before colonoscopy). A FC cut-off level ≥150 µg/g is considered indicative of endoscopic and/or histological activity, as well as of early clinical relapse, as previously demonstrated.[4-7] Following these assumptions, it is considered that a 100-point drop (µg/g) of FC as a clinically meaningful change.

A fecal sample from the first bowel movement in the morning is stored in a refrigerator at 2-8° C. for a maximum of 24 h before performing the analysis. Quantification of FC levels is carried out using a quantitative, enzyme-linked immunosorbent assay (Calprest; Eurospital, Trieste, Italy), according to the manufacturers' instructions. Standards with known concentrations of calprotectin are used as reference. Measurements will range from 15 to 3000 m/g.

All patients randomized to treatment who received at least 1 dose of the study drug are included in the intention-to-treat (ITT) analysis. Descriptive statistics are reported for each group (mean with standard deviation [SD] or median with interquartile range [IQR]); binary logistic regression analysis was performed to evaluate the primary, secondary and combined aims. Because a normal distribution of FC could not be presumed, a non-parametric Mann-Whitney U-test is used to compare differences in FC levels between groups at each time point, while analysis of variance with the Friedman test is used to assess FC changes from baseline to 3 and 6 months within each group. A post-hoc Wilcoxon signed-rank test with Bonferroni correction can be performed if the Friedman test achieved significance. The Kaplan-Meier method is used to estimate the relapse-free survival (RFS) for each treatment group at 3 and 6 months, and a Log-rank test is used to compare them. A p value less than 0.05 is considered significant. IBM SPSS version 23.0 (Chicago, Ill., USA) can be used to perform statistical analysis.

A comparison between the EPA-FFA group and the placebo group.

A clinical study demonstrating the beneficial effects of highly purified EPA-FFA in reducing mucosal inflammation, as indicated by FC levels, and in preventing symptomatic relapses in UC patients is conducted. The chosen primary endpoint is a decrease in FC level, as a marker of reduction of tissue inflammation suggestive of clinical remission. Notably, data in the published literature suggest that FC values <150 µg/g are indicative of low-grade histological activity.[4]

Recent epidemiological data indicate a potential beneficial effect of n-3 PUFAs in reducing the incidence of UC. Ananthakrishnan et al. prospectively analyzed cases of UC in a large cohort study conducted over 26 years (Nurses' Health Study) and found that a high intake of n-3 PUFAs was associated with a reduced risk of incident UC.[14] Moreover, consumption of a high ratio of pro-inflammatory n-6 PUFAs to n-3 PUFAs has been associated with an increased risk of UC.[15-19]

However, previous clinical trials of fish oil derivatives in UC have reported mixed results.[20,21] Despite some beneficial effects, such as a reduction of inflammation and a decreased need for steroid use, these studies failed to demonstrate a clear protective effect of fish oil derivatives in preventing clinical relapse. Possible explanations for these disparate results could be related to different study design, the formula of n-3 PUFAs used, too broad a range of dosages, poor patient adherence, the wrong time of administration, or the use of olive oil or other PUFAs as placebo.[22]

In the present study, active n-3 PUFAs is formulated as 2 g of highly purified EPA (>95%) in a free fatty acid (FFA) form, in gastric-resistant capsules. Previously, it has been demonstrated[23-25] that the FFA form of n-3 PUFAs provides the most favourable pharmacokinetic profile in comparison to ethyl ester and triglyceride preparations. Moreover, in a study of patients with IBD and healthy volunteers who received EPA-FFA 2 g daily for 8 weeks, EPA was consistently incorporated into plasma phospholipids and red blood cell membranes. EPA-FFA is quickly converted into docosahexaenoic acid via docosapentaenoic acid and EPA can be considered the "universal donor" of n-3 PUFAs.[26]

The level of FC is used as a surrogate of impending clinical relapse to select patients who are eligible for preventative treatment. Previously published robust data have already established that FC is a very reliable marker of mucosal inflammation, with a good correlation with endoscopic score[3, 5] and histological inflammation grade,[4] and ability to predict clinical relapse.[5-7] FC is increasingly being included in high-quality, well-designed clinical trials as a predictor of response to new treatments.[27] Although, the optimal FC cut-off level to identify patients at high risk of developing symptomatic relapse in the short term is still under debate, but published data,[6,7] indicated that 150 µg/g is a reasonable cut-off value for such purpose. It is believed that it is important to accurately identify patients at risk of relapse. Testing the level of FC provides a method to identify and treat a subgroup of patients before symptoms occurrence, reducing episodes of acute flares, hospitalization, need of more toxic drugs and patient's disability.

Mucosal and histological inflammation are predictors of a worsening UC course,[30] whereas low levels of FC predict sustained clinical remission.[31] In line with these findings, it is shown herein that a significant reduction of FC level is an important endpoint to reach in order to prolong a symptomless disease course. Notably, the concept that adding EPA-FFA to ongoing UC treatment could reduce mild mucosal inflammation and stabilize clinical activity of the disease. According to other studies in which FC was tested as a predictor of clinical course[6,7] and of the disease pattern, CRP did not change significantly throughout the period of the study, confirming its poor sensitivity in monitoring UC disease activity compared to FC.[33]

In conclusion, the use of EPA-FFA decreases fecal calprotectin level, an important inflammatory marker in UC, and is a safe and promising treatment to maintain symptom-free remission in UC patients.

REFERENCES

1 Langholz E, Munkholm P, Davidsen M, et al. Course of ulcerative colitis: Analysis of changes in disease activity over years. *Gastroenterology* 1994; 107: 3-11.

2 Sipponen T, Kolho K-L. Fecal calprotectin in diagnosis and clinical assessment of inflammatory bowel disease. *Scand J Gastroenterol* 2015; 50: 74-80.

3 Lobatón T, Rodriguez-Moranta F, Lopez A, et al. A New Rapid Quantitative Test for Fecal Calprotectin Predicts Endoscopic Activity in Ulcerative Colitis. Inflamm *Bowel Dis* 2013; 19: 1034-1042.

4 Guardiola J, Lobatón T, Rodriguez-Alonso L, et al. Fecal Level of Calprotectin Identifies Histologic Inflammation in Patients With Ulcerative Colitis in Clinical and Endoscopic Remission. *Clin Gastroenterol Hepatol* 2014; 12: 1865-1870.

5 Scaioli E, Scagliarini M, Cardamone C, et al. Clinical application of faecal calprotectin in ulcerative colitis patients. *Eur J Gastroenterol Hepatol* 2015; 27: 1418-1424.

6 Costa F, Mumolo M G, Ceccarelli L, et al. Calprotectin is a stronger predictive marker of relapse in ulcerative colitis than in Crohn's disease. *Gut* 2005; 54: 364-368.

7 García-Sánchez V, Iglesias-Flores E, González R, et al. Does fecal calprotectin predict relapse in patients with Crohn's disease and ulcerative colitis? *J Crohns Colitis* 2010; 4: 144-152.

8 Calder P C. Marine omega-3 fatty acids and inflammatory processes: Effects, mechanisms and clinical relevance. *Biochim Biophys Acta* 2015; 1851: 469-484.

9 Yaqoob P. Mechanisms underlying the immunomodulatory effects of n-3 PUFA. *Proc Nutr Soc* 2010; 69: 311-315.

10 Lev-Tzion R, Griffiths A M, Leder O, et al. Omega 3 fatty acids (fish oil) for maintenance of remission in Crohn's disease. Cochrane Database Syst Rev 2014; (2): CD006320.

11 Turner D, Shah P S, Steinhart A H, et al. Maintenance of remission in inflammatory bowel disease using omega-3 fatty acids (fish oil): a systematic review and meta-analyses. *Inflamm Bowel Dis* 2011; 17: 336-345.

12 MacLean C H, Mojica W A, Newberry S J, et al. Systematic review of the effects of n-3 fatty acids in inflammatory bowel disease. *Am J Clin Nutr* 2005; 82: 611-619.

13 Lee D, Albenberg L, Compher C, et al. Diet in the pathogenesis and treatment of inflammatory bowel diseases. *Gastroenterology* 2015; 148: 1087-1106.

14 Ananthakrishnan A N, Khalili H, Konijeti G G, et al. Long-term intake of dietary fat and risk of ulcerative colitis and Crohn's disease. *Gut* 2014; 63: 776-784.

15 Lewis J D, Abreu M T. Diet as a Trigger or Therapy for Inflammatory Bowel Diseases. *Gastroenterology* 2017; 152: 398-414.e6.

16 Schroeder K W, Tremaine W J, Ilstrup D M. Coated Oral 5-Aminosalicylic Acid Therapy for Mildly to Moderately Active Ulcerative Colitis. *N Engl J Med* 1987; 317: 1625-1629.

17 Daperno M, Castiglione F, de Ridder L, et al. Results of the 2nd part Scientific Workshop of the ECCO (II): Measures and markers of prediction to achieve, detect, and monitor intestinal healing in Inflammatory Bowel Disease. *J Crohns Colitis* 2011; 5: 484-498.

18 Geboes K, Riddell R, Ost A, Jensfelt B, et al. A reproducible grading scale for histological assessment of inflammation in ulcerative colitis. Gut 2000; 47: 404-409.

19 de Silva P S A, Olsen A, Christensen J, et al. An Association Between Dietary Arachidonic Acid, Measured in Adipose Tissue, and Ulcerative Colitis. *Gastroenterology* 2010; 139: 1912-1917.

20 De Ley M, de Vos R, Hommes D W, et al. Fish oil for induction of remission in ulcerative colitis. Cochrane Database Syst Rev 2007; (4):CD005986.

21 Cheifetz A S, Gianotti R, Luber R, et al. Complementary and alternative medicines used by patients with inflammatory bowel diseases. *Gastroenterology* 2017; 152: 415-29.e15.

22 Marion-Letellier R, Savoye G, Beck P L, et al. Polyunsaturated fatty acids in inflammatory bowel diseases: a reappraisal of effects and therapeutic approaches. *Inflamm Bowel Dis* 2013; 19: 650-661.

23 Belluzzi A, Brignola C, Campieri M, et al. Effects of new fish oil derivative on fatty acid phospholipid-membrane pattern in a group of Crohn's disease patients. *Dig Dis Sci* 1994; 39: 2589-2594.

24 el Boustani S, Colette C, Monnier L, et al. Enteral absorption in man of eicosapentaenoic acid in different chemical forms. *Lipids* 1987; 22: 711-714.

25 Davidson M H, Johnson J, Rooney M W, et al. A novel omega-3 free fatty acid formulation has dramatically improved bioavailability during a low-fat diet compared with omega-3-acid ethyl esters: the ECLIPSE (Epanova® compared to Lovaza® in a pharmacokinetic single-dose evaluation) study. *J Clin Lipidol* 2012; 6: 573-584.

26 Scaioli E, Cardamone C, Liverani E, et al. The pharmacokinetic profile of a new gastroresistant capsule preparation of eicosapentaenoic acid as the free fatty acid. *BioMed Res Int* 2015; 2015: 360825.

27 Sandborn W J, Panés J, Zhang H, et al. Correlation between concentrations of fecal calprotectin and outcomes of patients with ulcerative colitis in a phase 2 trial. *Gastroenterology* 2016; 150: 96-102.

28 Feagan B G, Sandborn W J, Mittmann U, et al. Omega-3 free fatty acids for the maintenance of remission in Crohn disease: the EPIC Randomized Controlled Trials. *JAMA* 2008; 299: 1690-1697.

29 Sahmoud T, Hoctin-Boes G, Modigliani R, et al. Identifying patients with a high risk of relapse in quiescent Crohn's disease. The GETAID Group. The Groupe d'Etudes Thérapeutiques des Affections Inflammatoires Digestives. *Gut* 1995; 37: 811-818.

30 Zenlea T, Yee E U, Rosenberg L, et al. Histology Grade Is Independently Associated With Relapse Risk in Patients With Ulcerative Colitis in Clinical Remission: A Prospective Study. *Am J Gastroenterol* 2016; 111: 685-690.

31 Mooiweer E, Severs M, Schipper M E I, et al. Low fecal calprotectin predicts sustained clinical remission in inflammatory bowel disease patients: a plea for deep remission. *J Crohns Colitis* 2015; 9: 50-55.

32 Prossomariti A, Scaioli E, Piazzi G, et al. Short-term treatment with eicosapentaenoic acid improves inflammation and affects colonic differentiation markers and microbiota in patients with ulcerative colitis. *Sci Rep* 2017; 7: 7458.

33 Vermeire S, Van Assche G, Rutgeerts P. Laboratory markers in IBD: useful, magic, or unnecessary toys? *Gut* 2006; 55: 426-431.

34 Molander P, Färkkilä M, Ristimäki A, et al. Does fecal calprotectin predict short-term relapse after stopping TNFα-blocking agents in inflammatory bowel disease patients in deep remission? *J Crohns Colitis* 2015; 9: 33-40.

What is claimed is:

1. A method of reducing fecal calprotectin levels and relapses in subjects with ulcerative colitis (UC), the method comprising administering to the subject a composition consisting of eicosapentaenoic acid as free fatty acids (EPA-FFA) having a purity of at least 95%, in a therapeutic amount effective to reduce levels of fecal calprotectin below 150 µg/g, an aminosalicylate (5-ASA), and a pharmaceutically acceptable carrier.

2. The method of claim 1, wherein the EPA-FFA has a purity of at least 99%.

3. The method of claim 2, wherein the EPA-FFA is formulated into pH-dependent, enteric-coated capsules for release of the contents in the small intestine at about pH 5.5.

4. The method of claim 1, wherein the levels of fecal calprotectin is reduced to about 110 µg/g or lower.

5. The method of claim 1, wherein the therapeutic amount is in an amount from about 250 mg to 4 g per day.

6. The method of claim 1, wherein the therapeutic amount is in an amount from about 1000 mg to about 2 g per day.

7. The method of claim 6, wherein the therapeutic amount is administered daily or weekly for about 1 to 8 months.

8. The method of claim 1, wherein the aminosalicylate is selected from sulfasalazine, mesalamine, olsalazine, and balsalazide.

9. A method for reducing fecal calprotectin levels and relapses in subjects with ulcerative colitis (UC), the method comprising administering to the subject a composition consisting of eicosapentaenoic acid as free fatty acids (EPA-FFA) having a purity of at least 95%, in a therapeutic amount effective to reduce levels of fecal calprotectin below 150 µg/g, and an aminosalicylate (5-ASA).

10. The method of claim 9, wherein the EPA-FFA has a purity of at least 99%.

11. The method of claim 9, wherein the levels of fecal calprotectin is reduced to about 110 µgig or lower.

12. The method of claim 9, wherein the therapeutic amount is in an amount from about 250 mg to 4 g per day.

13. The method of claim 8, wherein the therapeutic amount is in an amount from about 1000 mg to about 2 g per day.

14. The method of claim 13, wherein the therapeutic amount is administered daily or weekly for about 1 to 8 months.

15. The method of claim 9, wherein the aminosalicylate is selected from sulfasalazine, mesalamine, olsalazine, and balsalazide.

\* \* \* \* \*

UNITED STATES PATENT AND TRADEMARK OFFICE
CERTIFICATE OF CORRECTION

PATENT NO. : 11,013,709 B2
APPLICATION NO. : 16/535536
DATED : May 25, 2021
INVENTOR(S) : Justin Slagel It is certified that error appears in the above-identified patent and that said Letters Patent is hereby corrected as shown below:

Claim 11, Column 11, Line 14:
calprotectin is reduced to about 110 μgig or lower.
Should read:
calprotectin is reduced to about 110 μg/g or lower.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*